(12) United States Patent
Wolozin

(10) Patent No.: US 6,472,421 B1
(45) Date of Patent: *Oct. 29, 2002

(54) METHODS FOR TREATING, PREVENTING, AND REDUCING THE RISK OF THE ONSET OF ALZHEIMER'S DISEASE USING AN HMG COA REDUCTASE INHIBITOR

(75) Inventor: Benjamin Wolozin, Hinsdale, IL (US)

(73) Assignee: Nymox Corporation, St. Laurent (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 38 days.

(21) Appl. No.: 09/190,439

(22) Filed: Nov. 13, 1998

(51) Int. Cl.⁷ .................. A61K 31/35; A61K 31/21; A61K 31/235
(52) U.S. Cl. .................. 514/451; 514/455; 514/510; 514/543
(58) Field of Search .................. 514/455, 451, 514/510, 543

(56) References Cited

U.S. PATENT DOCUMENTS

| | | | |
|---|---|---|---|
| 5,734,054 A | 3/1998 | Dolle, III et al. ........... | 514/390 |
| 5,965,553 A | * 10/1999 | Bell et al. ................... | 514/211 |
| 6,080,778 A | 6/2000 | Yankner et al. ............. | 514/451 |

FOREIGN PATENT DOCUMENTS

| | | |
|---|---|---|
| EP | 0 179 559 | 4/1986 |
| EP | 0 569 777 | 11/1993 |
| WO | 95/06470 | 3/1995 |
| WO | 97/48701 | 12/1997 |
| WO | WO 98/47518 | 10/1998 |
| WO | WO 99/38498 | 8/1999 |
| WO | WO 99/48488 | 9/1999 |

OTHER PUBLICATIONS

Graul A., et al., "Atorvastatin Calcium", Drugs of the Future, vol. 22(9), pp. 956–968 (1997).

Yankner Bruce A., "Mechanisms of Neuronal Degeneration in Alzheimer's Disease", Neuron, vol. 16, pp. 921–932, (May 1996).

* cited by examiner

Primary Examiner—Theodore J. Criares
(74) Attorney, Agent, or Firm—Foley & Lardner

(57) ABSTRACT

Described are methods for treating, preventing, or reducing the risk of the onset of Alzheimer's disease by administering a therapeutically effective amount of an inhibitor of the enzyme 3-hydroxy-3-methylglutaryl coenzyme A reductase ("HMG CoA reductase inhibitor") to a patient who is at risk for a coronary or cerebrovascular event or at risk for Alzheimer's disease.

22 Claims, No Drawings

METHODS FOR TREATING, PREVENTING, AND REDUCING THE RISK OF THE ONSET OF ALZHEIMER'S DISEASE USING AN HMG COA REDUCTASE INHIBITOR

FIELD OF THE INVENTION

This invention relates to methods of treating, preventing, and reducing the risk of Alzheimer's disease by administering a 3 beta-hydroxy-3 beta-methyl glutaryl CoA reductase inhibitor ("HMG CoA reductase inhibitor") to a patient in need of treatment.

BACKGROUND OF THE INVENTION

Alzheimer's disease ("AD") is a major cause of dementia among the elderly throughout the world. Beginning at age 65, the incidence of the disease rises steadily until by age 85, where conservative estimates place its rate of incidence at some 30% of that population. It is generally believed that the disease begins a number of years before it manifests itself in the mild cognitive changes that are the early signs of AD. Thus, the at risk population is believed to be 60 years or older.

The consequences of this disease are devastating, both to the patient and his or her family and care givers. The disease typically results in an inexorable decline in cognitive functions often coupled with gross behavioral changes, leading to the patient's inability to care for his or herself in the community and increased burdens on care givers and home care and nursing home providers. As the baby-boom generation enters the age of risk for Alzheimer's disease, the social and economic consequences of this disease loom even larger.

HMG CoA Reductase Inhibitors

HMG CoA reductase is the enzyme catalyzing the early rate-limiting step in cholesterol biosynthesis, i.e., conversion of HMG-CoA to mevalonate. Cholesterol and triglycerides circulate in the bloodstream as part of lipoprotein complexes. These complexes can be separated by density ultracentrifugation into high (HDL), intermediate (IDL), low (LDL), and very low (VLDL) density lipoprotein fractions. Triglycerides (TG) and cholesterol synthesized in the liver are incorporated into VLDLs and released into the plasma for delivery to pheripheral tissues. In a series of subsequent steps, VLDLs are transformed into IDLs and cholesterol-rich LDLs. HDLs, containing apolipoprotein A, are hypothesized to participate in the reverse transport of cholesterol from tissues back to the liver.

Clinical and pathological studies have shown that elevated levels of total cholesterol, low LDL-cholesterol (LDL-C), and apolipoprotein B (a membrane transport protein for LDL) promote human atherosclerosis. Similarly, decreased levels of HDL-cholesterol (HDL-C) and its transport complex, apolipoprotein A, are associated with the development of atherosclerosis. Epidemiologic investigations have established that cardiovascular morbidity and mortality vary directly with the level of total cholesterol and LDL-C, and inversely with the level of HDL-C. Thus, HDLs have been characterized as "good" lipoproteins, while cholesterol-rich LDLs have been characterized as being less favorable.

Elevated serum total cholesterol is closely related to the development of cardiovascular, cerebrovascular, and peripheral vascular disorders. Hypercholesterolemia has been linked to increased risk of coronary heart disease. Many studies have found that a reduction of elevated serum cholesterol levels leads to a decreased incidence of coronary disease.

HMG CoA reductase inhibitors have been shown to reduce total serum cholesterol levels, LDL-C, and apolipoprotein B, most likely by increasing the fractional catabolic rate of LDL and the liver's extraction of LDL precursors, blocking enzymes that synthesize cholesterol, and simultaneously increasing the levels of HDL. Lipid lowering drugs, such as HMG CoA reductase inhibitors, have been used successfully to lower serum cholesterol levels when diet and lifestyle changes have proven inadequate and have been shown to reduce the incidence of both cardiovascular and cerebrovascular events.

Many references teach the use of HMG CoA reductase inhibitors for treating coronary disease. For example, U.S. Pat. No. 5,831,115, for "Inhibitors of squalene synthase and protein farnesyltransferase," describes lipid-lowering compositions comprising an HMG CoA reductase inhibitor; U.S. Pat. No. 5,807,834, for "Combination of a cholesterol absorption inhibitor and a cholesterol synthesis inhibitor," teaches that HMG CoA reductase inhibitors are known to be useful for the treatment of hypercholesterolemia; U.S. Pat. No. 5,801,143, for "Cyclic depsipeptides useful for treatment of hyperlipemia," teaches that HMG CoA reductase inhibitors are known to exhibit a remarkable lowering of cholesterol and are useful in treating hypercholesterolemia; U.S. Pat. No. 5,798,375, for "Treatment of arteriosclerosis and xanthoma," teaches the use of HMG CoA reductase inhibitors for treating arteriosclerosis and xanthoma; and U.S. Pat. No. 5,786,485, for "Optically active beta-aminoalkoxyborane complex," notes that HMG CoA reductase inhibitors are known to be antihyperlipemia agents.

Relationship Between Alzheimer's Disease and Cholesterol Levels

While Alzheimer's disease is typically characterized pathologically by the presence of senile plaques and neurofibrillary tangles found at autopsy in the brains of patients afflicted with the disease, vascular components of the disease have also been noted. These include lesions in the cerebral microcirculation and vascular deposits of Aβ protein, which is also a major constituent of the senile plaques found in AD.

In addition to a relationship with coronary disease, it is known that there is a relationship between serum cholesterol levels and the incidence and the pathophysiology of AD. Epidemiological studies show that patients with elevated cholesterol have an increased risk of AD. (Notkola et al., "Serum total cholesterol, apolipoprotein E epsilon 4 allele, and Alzheimer's disease," *Neuroepidemiology;* 17(1): 14–20 (1998); Jarvik et al., "Interactions of apolipoprotein E genotype, total cholesterol level, age and sex in prediction of Alzheimer's disease: a case-control study," *Neurology,* 45(6):1092–6 (1995).) Other studies have established that patients possessing the apolipoprotein ε4 genotype ("apoE4") that codes for a variant of apolipoprotein, a cholesterol transport protein, have an increased risk for AD, as well as for elevated levels of cholesterol and for heart disease. (Mahley R, "Cholesterol transport protein with expanding role in cell biology," *Science,* 240:622–630 (1988); Saunders et al., "Association of apolipoprotein E allele ε4 with late-onset familial and sporadic Alzheimer's disease," *Neurology,* 43:1467–1472 (1993); Corder et al., "Gene dose of apolipoprotein E type 4 allele and the risk of Alzheimer's disease in late-onset families," *Science,* 261:921–923 (1993); Jarvik et al., "Coronary artery disease, hypertension, ApoE and cholesterol: a link to Alzheimer's disease?" *Annals of the New York Academy of Sciences,* 826:128–146 (1997).) Both apoE4 and a second putative risk factor for AD, α-2-macroglobulin, bind to a receptor, the lipoprotein receptor related protein, which is important for cellular uptake of cholesterol. (Narita et al., "Alpha2-macroglobulin complexes with and mediates the endocytosis of beta-amyloid peptide via cell surface low-density lipoprotein receptor-related protein," *Journal of Neurochemistry;* 69(5):1904–11 (1997); and Blacker et al., "Alpha-2 macroglobulin is genetically associated with Alzheimer's disease," *Nat. Gen.,* 19:357–60 (1998).) Other studies have shown that cholesterol increases the production of Aβ protein, which accumulates in the brains of patients with AD and is thought by many researchers to cause the neurodegeneration underlying the disease. (Selkoe D J, "Cell biology of the beta-amyloid precursor protein and the genetics of Alzheimer's disease," *Cold Spring Harbor Symposia on Quantitative Biology,* 61:587–96 (1996); and Simons et al., "Cholesterol depletion inhibits the generation of β-amyloid in hippocampal neurons," *Proc. Natl. Acad. Sci., USA,* 95:6460–4 (1998).)

While it was known that there is a connection between serum cholesterol levels and the incidence and the pathophysiology of AD, there remains a need in the art for effective methods of treating, preventing, and reducing the risk of AD. This invention satisfied these needs.

SUMMARY OF THE INVENTION

This invention is directed to the surprising discovery that HMG CoA reductase inhibitors are useful in treating, preventing, and reducing the risk of AD. The methods of the invention comprise preventing the onset of AD, reducing the risk of the onset of AD, and treating the presence of AD through the administration of therapeutically effective doses of one or more HMG CoA reductase inhibitors.

HMG CoA reductase inhibitors are known in the art. Preferred CoA reductase inhibitors to be used in the methods of the invention are lovastatin and pravastatin, although the invention is not limited to the use of these two compounds.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention provides methods for treating the presence of AD, preventing the onset of AD, and reducing the risk of AD through the administration of therapeutically effective doses of one or more HMG CoA reductase inhibitors. This invention is predicated on the surprising and unexpected discovery that patients who are over the age of 60 and, therefore, fall within the population at risk for AD, and who have been treated with one or more HMG CoA reductase inhibitors, exhibit a marked reduction in the prevalence of AD as compared to the total patient population. In addition, it was also surprisingly discovered that such patients also exhibit a marked reduction in the prevalence of AD as compared to patients taking other medications typically prescribed in the treatment of cardiovascular disease.

Preferably, the invention comprises preventing the onset of AD, or reducing the risk of AD, within twelve months of beginning treatment with one or more HMG CoA reductase inhibitors. More preferably, the invention comprises preventing the onset of AD, or reducing the risk of AD, within six months of beginning treatment with one or more HMG CoA reductase inhibitors. Such prevention or reduction is shown by the results Example 3, where at one testing site, an almost 90% decrease in the onset of AD was observed following treatment with one or more HMG CoA reductase inhibitors. When the results from the three testing sites of Example 3 were combined, a dramatic and unexpected reduction of 69.6% in the risk of AD was shown upon administration of or more HMG CoA reductase inhibitors.

Preferred HMG CoA reductase inhibitors are lovastatin and pravastatin. Surprisingly, it was discovered that not all HMG CoA reductase inhibitors have an effect on the prevalence of AD. As described in the examples below, patients taking simavastatin did not exhibit a significant reduction in incidence of AD. Simvastatin is an HMG CoA reductase inhibitor having a similar efficacy in lowering cholesterol levels as lovastatin and pravastatin, and having a better ability to cross the blood-brain barrier than pravastatin.

Moreover, it was unexpectedly discovered that while some HGM CoA reductase inhibitors exhibit a dramatic reduction in degree and prevalence of AD, patients taking other types of drugs used to treat cardiovascular disorders, such as beta blockers, furosemide, and captopril, did not show any significant reduction in the prevalence or degree of AD. In fact, patients taking beta blockers had a prevalence of AD some 40% above the total patient cohort, consistent with prior reports that risk factors for heart disease increase the risk of AD. Thus, while there is a connection between vascular changes and AD, it appears that this is not the only mechanism functioning to affect the prevalence and degree of AD upon administration of one or more HMG CoA reductase inhibitors.

Target Population

There are several target populations that can benefit from treatment according to the present invention.

A first target patient population for this invention is those patients having one or more risk factors for cardiovascular and/or cerebrovascular disease. The term "risk factor for cardiovascular or cerebrovascular disease" is defined as risk factors such as hypercholesterolemia, hypertension, diabetes, cigarette smoking, familial or previous history of coronary artery disease, cerebrovascular disease, cardiovascular disease, and being male. Hypercholesterolemia in this context means the patient's serum total cholesterol concentration is at least 5.2 mmol/liter (at least 200 mg/dl), and more preferably the patient's serum total cholesterol concentration is from about 200 to about 300 mg/dl. The term "cerebrovascular disease" includes such diseases as atherosclerosis of the intracranial and/or extracranial arteries, stroke, syncope, and transient ischemic attacks. The term "cardiovascular disease" includes such diseases as atherosclerosis of the coronary arteries, angina pectoris, myocardial infarction, sudden cardiac death, and heart failure.

A second target patient population for this invention is those patients at risk for AD. The term "at risk for AD" is defined as patients being over the age of 60 or patients having a predisposition for AD. AD predisposing factors identified or proposed in the scientific literature include (but are not limited to): (1) a genotype predisposing a patient to AD; (2) environmental factors predisposing a patient to AD; (3) past history of infection by viral and bacterial agents predisposing a patient to AD; and (4) vascular factors predisposing a patient to AD.

At present, a number of genotypes are thought to predispose a patient to AD. These include the rare genotypes such as presenilin-1, presenilin-2, and amyloid precursor protein (APP) missense mutations which lead to some forms of familial early-onset AD, and the more common genotypes such as apoE4 and α-2-macroglobulin genotypes, both of which are thought to increase the risk of acquiring sporadic late-onset AD. In addition, there is evidence that a family history of AD increases the risk of acquiring AD. Environmental factors have been proposed as predisposing a patient to AD, including exposure to aluminum, although the epidemiological evidence linking AD to environmental factors is more controversial. In addition, prior infection by a number of viral and bacterial agents has been suggested as predisposing a patient to AD, including the herpes simplex virus and chlamydia pneumoniae. Finally, other predisposing factors for AD can include risk factors for cardiovascular and/or cerebrovascular disease, including cigarette smoking, hypertension and diabetes. "At risk for AD" also encompasses any other predisposing factors not listed above or as yet identified and includes an increased risk for AD caused by head injury, medications, diet, or lifestyle.

A third target population for this invention is any patient, regardless of whether the patient has a risk factor for cardiovascular and/or cerebrovascular disease, or whether the patient is at risk for AD. The goal of treating such a target population is to reduce that patient's risk for developing AD in the future.

A fourth target population for this invention is any mammalian species, such as dogs, cats, horses, cattle, etc.

Suitable HMG CoA Reductase Inhibitors

The term, "HMG CoA reductase inhibitor," refers to any compound which inhibits the bioconversion of 3-hydroxy-3-methylglutaryl coenzyme A to mevalonic acid catalyzed by the enzyme HMG CoA reductase. The inhibiting effect of any such compounds can be readily determined by those skilled in the art according to standard assays. This invention describes and references a number of HMG CoA reductase inhibitors. However, other HMG CoA reductase inhibitors will be known to those skilled in the art.

The HMG CoA reductase inhibitors suitable for use in the invention include, but are not limited to, pravastatin and related compounds, as disclosed in U.S. Pat. No. 4,346,227; and lovastatin and related compounds, as disclosed in U.S. Pat. No. 4,231,938. The disclosures of U.S. Pat. Nos. 4,346,227 and 4,231,938 are specifically incorporated by reference. Lovastatin and pravastatin are preferred HMG CoA reductase inhibitors for use in the invention.

Lovastatin, marketed under the trade name Mevacor®, has an empirical formula of $C_{24}H_{36}O_5$. Following is the structure of lovastatin in its beta-hydroxyacid form, which is the form that is a competitive inhibitor of HMG CoA reductase:

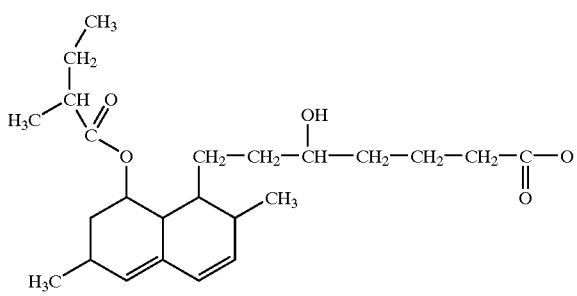

Pravastatin, marketed under the trade name Pravachol®, is designated chemically as 1-naphthalene-hepatnoic acid, 1,2,6,7,8,8a-hexahydro-β,δ,6-trihydroxy-2-methyl-8-(2-methyl-1 -oxobutoxy).

Other HMG CoA reductase inhibitors which may be employed in the invention include, but are not limited to, velostatin, atorvastatin (Lipitor®) and other 6-[2-(substituted-pyrrol-1-yl)alkyl]pyran-2-ones and derivatives, as disclosed in U.S. Pat. No. 4,647,576; fluvastatin (Lescol®); fluindostatin (Sandoz XU-62-320); pyrazole analogs of mevalonolactone derivatives as disclosed in PCT application WO 86/03488; rivastatin and other pyridyldihydroxyheptenoic acids as disclosed in European Patent 491226A; Searle's SC-45355 (a 3-substituted pentanedioic acid derivative) dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-di-substituted pyrrole, furan, and thiophene derivatives, as disclosed in European Patent Application No. 0221025; naphthyl analogs of mevalonolactone, as disclosed in U.S. Pat. No. 4,686,237; octahydronaphthalenes, such as those disclosed in U.S. Pat. No. 4,499,289; keto analogs of mevinolin (lovastatin), as disclosed in European Patent Application No. 0,142,146 A2; as well as other HMG CoA reductase inhibitors.

In addition, phosphinic acid compounds useful in inhibiting HMG CoA reductase suitable for use herein are disclosed in U.S. Pat. No. 4,904,646, which compounds have the moiety:

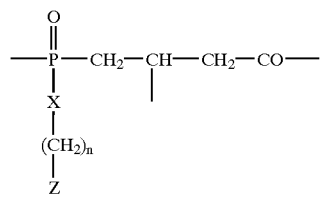

wherein X is —O— or —NH—, n is 1 or 2, and Z is a hydrophobic anchor.

Another class of HMG CoA reductase inhibitors suitable for use herein include phosphinic acid components disclosed in U.S. Pat. No. 5,091,378, which compounds have the moiety:

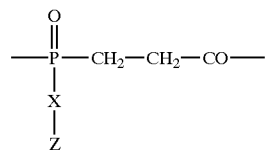

wherein X is selected from the group consisting of —CH$_2$—, —CH$_2$—CH$_2$—, —CH CH—, —CH$_2$CH$_2$CH$_2$—, —C≡C—, and CH$_2$O—, where O is linked to Z, and Z is a hydrophobic anchor.

Some of the active substances described above form commonly known, pharmaceutically acceptable salts, such as alkali metal and other common basic salts, or acid addition salts, etc. References to the base substances are therefore intended to include such common salts known to be substantially equivalent to the parent compound.

One of ordinary skill in the art can use various screening methods to identify HMG CoA reductase inhibitors useful in the methods of the invention. One example of a useful screening method is a clinical record database analysis, as described below in Example 3. This method comprises identifying large clinical record databases (20,000 patients or more) created and maintained by one medical organization, such as a medical center, health maintenance organization, or a preferred provider organization. The database should be organized as a relational database that permits the efficient sorting and analyzing of the patient records and record entries by computer. The individual patient records should contain pertinent demographic information, such as age and gender, and use standardized coding of diagnoses, such as the ICD-9-CM system. Each patient record should contain entries detailing the medications the patient has received and, preferably, but not necessarily, for how long the medication was administered, the dosage of the medication, and the illness for which the medication was prescribed.

Preferably, but not necessarily, the medical organization that maintains the database has a quality of care assurance program to ensure adherence to minimum standards of diagnosis and care as well as standards of record-keeping. Ideally, such quality of care assurance programs include periodic performance assessments of all physicians attending upon or treating the patients served by the medical organization. Many health maintenance organizations, hospitals, preferred provider organization, and other medical organizations have such quality of care assurance programs to maintain standards of health care for their patients while tracking and managing costs.

The database is screened to determine which records relate to patients who have received active treatment and for which there is a diagnosis. Preferably, the physician or physicians who diagnose patients with AD are identified and interviewed to determine the criteria used for the diagnosis of AD and the code used in the database to identify that diagnosis.

The method of analyzing the clinical record database to identify HMG CoA reductase inhibitors useful in the methods of the invention comprises searching and sorting the database to identify those patients taking the HMG CoA reductase inhibitor to be screened and tracking whether the patient record discloses a diagnosis of AD. Preferably, the patients identified should be over the age of 60, which would enable study of a population in which the incidence and risk of AD is significant. The period of tracking of the patients should be reasonably uniform. AD should be diagnosed using criteria commonly accepted in the medical community and in a reasonably uniform manner for the patients in the database.

The incidence of AD in the patient population taking the HMG CoA reductase inhibitor being screened is then compared to other patient populations taking either other HMG CoA reductase inhibitors known to have no effect on the prevalence of AD, such as simvastatin, or other medications for hypertension, heart disease, or elevated cholesterol levels, as well as control groups of patients not taking these types of drugs.

Appropriate controls can be designed in a manner known to one of ordinary skill in the art. Example 3 below sets out two exemplary types of controls for such studies. The prevalence of AD for each of the populations can be calculated and analyzed statistically using methods known to one of ordinary skill in the art. A marked reduction in the prevalence of AD in a population taking the HMG CoA reductase inhibitor being screened as compared to a control or as compared to other HMG CoA reductase inhibitors known to have no effect on the prevalence of AD identifies the inhibitor as useful in the methods of the invention.

Other screening methods known to one of ordinary skill in the art to identify HMG CoA reductase inhibitors useful in the methods of the invention include the use of in vitro screening systems to identify HMG CoA reductase inhibitors that can inhibit the secretion of A$\beta$ and/or protect against the neurotoxicity of A$\beta$ protein, in vivo transgenic mouse models, and standard clinical trials designed to test the efficacy and safety of proposed treatments or medications for AD.

Many references teach methods of in vitro screening of potential therapeutics for AD. For example, U.S. Pat. No. 5,721,106, for "In Vitro method for screening beta-amyloid deposition," teaches methods for screening agents that enhance or inhibit beta-amyloid aggregation or deposition onto tissue; U.S. Pat. No. 5,547,841, for "In vitro method for screening for drugs that inhibit production or degradation of human A4-amyloid," describes an in vitro method of screening for drugs that are potentially useful for treatment of Alzheimer's Disease; U.S. Pat. No. 5,441,870, for "Methods for monitoring cellular processing of beta-amyloid precursor protein in vitro," describes how to monitor the secretion of beta-amyloid from cultured cells to identify inhibitors of beta-amyloid production; U.S. Pat. No. 5,538,845, for "Beta-amyloid peptide production inhibitors and methods for their identification," describes how to identify likely candidates for use as drugs for treating beta-amyloid diseases, such as Alzheimer's disease; and U.S. Pat. No. 5,605,811, for "Methods and compositions for monitoring cellular processing of beta-amyloid precursor protein," notes that the cultured cells described therein can be used in testing for compounds that cause a change in the secreted amount of the soluble fragment of beta APP.

Many references teach methods of in vivo screening of potential therapeutics for AD. For example, U.S. Pat. No. 5,811,633, for "Transgenic mouse expressing $APP_{770}$," teaches how transgenic mice, or mouse cells, are used to screen for compounds altering the pathological course of Alzheimer's Disease; U.S. Pat. No. 5,387,742, for "Transgenic mice displaying the amyloid-forming pathology of Alzheimer's disease," notes how the transgenic mice described therein provide useful models for studying compounds being tested for their usefulness in treating Alzheimer's disease; and U.S. Pat. No. 5,720,936, for "Transgenic mouse assay for compounds affecting amyloid protein processing," describes the construction of transgenic animal models for testing potential treatments for Alzheimer's disease.

Compositions to Be Administered

The one or more HMG CoA reductase inhibitors may be administered in a conventional systemic dosage form, such as a tablet, capsule, elixir, or injectable formulation. Oral dosage forms are preferred, although parenteral forms are satisfactory. The dose, route of administration, dosage form, regimen, and desired result are tailored to the age, weight, and condition of the patient.

For oral administration, the dosages indicated in the Physician'Desk Reference for pravastatin or lovastatin may be used for the administered HMG CoA reductase inhibitor. These dosages are in the range of about 1 to about 2000 mg per day in single or divided doses, and preferably from about 4 to about 200 mg per day in single or divided doses.

A preferred oral dosage form, such as tablets or capsules, contains the one or more HMG CoA reductase inhibitors in an amount preferably from about 0.5 to about 100 mg, more preferably from about 5 to about 80 mg, and most preferably from about 10 to about 40 mg. The remainder of the tablet or capsule can contain a physiologically acceptable carrier or other materials according to accepted pharmaceutical practice. Preferred dosages of various HMG CoA reductase inhibitors are known in the art and are described in, for example, U.S. Pat. No. 5,807,834. Tablets can be scored to provide for fractional doses. Liquid formulations can also be prepared by dissolving or suspending active substances in a conventional liquid vehicle acceptable for pharmaceutical administration so as to provide the desired dosage.

The formulations described herein above are administered for as long as the patient (1) has a risk factor for cardiovascular and/or cerebrovascular disease, or (2) is at risk for AD, or (3) continues to manifest the symptoms, signs, or biomarkers of AD. Sustained release forms of such formulations, which can provide such amounts biweekly, weekly, monthly, and the like, may also be employed. A dosing period of at least one to two weeks is required to achieve minimal benefit and to monitor the effect of the medication on the patient.

Suitable Excipients

Pharmaceutical compositions according to the invention may also comprise one or more binding agents, filling agents, lubricating agents, suspending agents, sweeteners, flavoring agents, preservatives, buffers, wetting agents, disintegrants, and other excipients. Such excipients are known in the art.

Examples of filling agents are lactose monohydrate, lactose hydrous, and various starches; examples of binding agents are various celluloses and cross-linked polyvinylpyrrolidone. Suitable lubricants are colloidal silicon dioxide, such as Aerosil 200; talc, stearic acid, magnesium stearate, calcium stearate, and silica gel. Examples of sweeteners are any natural or artificial sweetener, such as sucrose, xylitol, sodium saccharin, cyclamate, aspartame, and acsulfame. Examples of flavoring agents are Magnasweet (trademark of MAFCO), bubble gum flavor, and fruit flavors, and the like. Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel pH101, Avicel pH 102, and Avicel pH12; lactose such as lactose monohydrate, lactose anhydrous, and Pharmatose DCL21; dibasic calcium phosphate such as Emcompress; mannitol; starch; sorbitol; sucrose; and glucose. Suitable disintegrants include lightly crosslinked polyvinyl pyrrolidone, corn starch, potato starch, maize starch, and modified starches, croscarmellose sodium, cross-povidone, sodium starch glycolate, alginic acid or the like, and mixtures thereof.

A capsule may contain, in addition to the types of material listed above, a liquid carrier such as a fatty oil. Various other materials may be present as coatings or to otherwise modify the physical form of the dosage unit. For example, tablets or capsules may be coated with shellac, sugar, or both. A syrup of elixir may contain the active compound, water, alcohol or the like as the carrier, glycerol as solubilizer, sucrose as sweetening agent, methyl and propyl parabens as preservatives, a dye, and a flavoring such as cherry or orange.

The following examples are given to illustrate the present invention. It should be understood, however, that the invention is not to be limited to the specific conditions or details described in these examples.

EXAMPLE 1

The purpose of this example is to describe the preparation of tablets comprising lovastatin.

Lovastatin tablets can be prepared using conventional pharmaceutical techniques. As described in the *Physician Desk Reference,* pp. 1742 (Medical Economics Co., Inc., 1997), such tablets contain 10 mg, 20 mg, or 40 mg of the active agent, lovastatin, and the inert ingredients cellulose, lactose, magnesium stearate, starch, and butylated hydroxyanisole as a preservative. The tablets may also contain red ferric oxide, yellow ferric oxide, FD&C Blue 2, and FD&C Yellow 10 as coloring additives.

The lovastatin tablets may be employed to prevent or reduce the risk of AD or to treat AD in accordance with this invention.

EXAMPLE 2

The purpose of this example is to describe the preparation of tablets comprising pravastatin.

Pravastatin tablets can be prepared using conventional pharmaceutical techniques. As described in the *Physician Desk Reference,* pp. 770 (Medical Economics Co., Inc., 1997), such tablets contain 10 mg, 20 mg, or 40 mg of the active agent, pravastatin, and the inert ingredients croscarmellose sodium, lactose, magnesium oxide, magnesium stearate, microcrystalline cellulose, and povidone. The tablets may also contain red ferric oxide, yellow ferric oxide, and green lake blend as coloring additives The pravastatin tablets may be employed to prevent or reduce the risk of AD or to treat AD in accordance with this invention.

EXAMPLE 3

The purpose of this example is to demonstrate the effectiveness of treating, preventing, reducing the risk of AD by administering one or more HMG CoA reductase inhibitors to a patient in need.

A large study employing health care databases at three different hospitals in the United States examined the relationship between the frequency of AD and eight different medications, including the HMG CoA reductase inhibitors lovastatin (Mevacor®), pravastatin (Pravachol®), and simvastatin (Zocor®) ("Decreased Risk of Alzheimer's Disease Associated with HMG CoA Reductase Inhibitors," B. Wolozin et al., in press).

As described below, the results of the study show a marked decrease in the frequency of AD in patients over the age of 60 taking lovastatin, pravastatin, or a combination thereof. Surprisingly, patients over the age of 60 taking simvastatin had a prevalence of AD that did not differ significantly from that of the total patient population or that of patients taking captopril or furosemide. Patients taking atenolol (a β-adrenergic blocking agent), metoprolol (a β-adrenergic blocking agent), or propanolol (a β-adrenergic antagonist), either separately or in a combination of β-blocker drugs in general, had a prevalence of AD that was higher than that of the total patient cohort, confirming prior reports that risk factors associated with heart disease are also risk factors for AD.

Methods

To perform the study, relational databases at three different hospitals (Loyola Medical Center ("Loyola"), Hines Veterans Authority Medical Center ("Hines"), and Phoenix Veterans Authority Medical Center ("Phoenix")) were searched to obtain aggregate data about the frequency of AD. Each database included clinical information that facilitated identification of potential relationships between specific items. The databases were independent and did not overlap. Patient privacy was protected by using only aggregate patient data.

Each database was sorted to exclude any subjects under the age of 60 and any entries that contained patients' names but no medical information pertinent to the study. This yielded a total patient sample size for the three databases of 63,296 patients.

Each database was then sorted based on eight different medications (Table 1): lovastatin, pravastatin, simvastatin, captopril, furosemide, atenolol, metoprolol, and propanolol. The frequency of AD for each medication was then determined using ICD-9-CM codes.

ICD-9-CM codes are standard diagnostic codes. The National Center for Health Statistics (NCHS) developed the ICD-9-CM codes (the International Classification of Diseases, Ninth Revision, Clinical Modification codes) for use in the United States based on the World Health Organization's International Classification of Diseases. ICD-9-CM is a classification system that groups related disease entities and procedures for the reporting of statistical information. ICD-9-CM uses include the classification of morbidity and mortality information for statistical purposes, the indexing of hospital records by disease and operations, the reporting of diagnosis by physicians, data storage and retrieval, the calculation of hospital reimbursement under the Social Security Act, and the reporting and compiling of health care data to assist in evaluating the appropriateness and timeliness of medical care, planning health care delivery systems, determining patterns of care among health care providers, analyzing payments for health services and conducting epidemiological and clinical research. The NCHS and the Health Care Financing Administration maintain the ICD-9-CM codes.

Alzheimer's disease was identified under the ICD-9-CM code of 331.0, but because other codes also apply to AD, the codes 331.2, 290.0, 290.10–13, 290.20 and 290.3 were also included as AD cases based on interviews with the physicians at each center who diagnosed or oversaw the diagnosis of patients with AD and on their coding practices for AD. The diagnosis of AD was made according to the criteria of the National Institute of Neurological and Communicative Disorders and Stroke (NINCDS) and the Alzheimer's Disease and Related Disorders Association (ADRDA) Work Group (McKhann et al., "Clinical Diagnosis of Alzheimer's Disease: Report of the NINCDS-ADRDA Work Group under the Auspices of Department of Health and Human Services Task Force on Alzheimer's Disease," *Neurology*, 34:939–944 (1984).) Each AD patient had received either a CT scan or MRI to exclude other diagnoses, and had been screened for other metabolic, toxic, or affective disorders that may produce dementia. In addition, all AD patients at the Phoenix and Loyola centers had a mini-mental score of 24 or lower (Folstein et al., "Mini-Mental State," A Practical Method For Grading The Cognitive State of Patients For The Clinican, *J. Psychiat. Res.*, 12:189–198 (1975)), and at the Hines center all patients for whom a mini-mental test was available similarly had scores of 24 or less.

To control for selection biases, such as the tendency of internists to refer patients for neurological work-ups, the risk of transient ischemic attacks (TIAs) were also determined for each of the eight different medications using the ICD-9-CM codes 434.00, 433.00, 433.10, 433.20. 435.0, and 435.1–3.

Statistics were determined by comparisons of proportions using chi square analyses. All statistics listed P values and 95% confidence intervals.

Results

The results of the study are summarized in Table I.

TABLE I

Comparison of rates of AD with Administration of Various Medications

| Medication | # of Patients | Mean Age | Prevalence Of AD/1000 Combined | Prevalence Of AD/1000 Hines | Prevalence Of AD/1000 Loyola | Prevalence Of AD/1000 Phoenix | Std Error | Significance vs. Lovastatin + Pravastatin | Confidence Intervals |
|---|---|---|---|---|---|---|---|---|---|
| Lovastatin | 4180 | 71 ± 1 | 3.6 | 2.5 | 6.4 | 8.2 | 0.002 | | |
| Pravastatin | 2326 | 72 ± 1 | 4.3 | 1.1 | 0 | 8.3 | 0.002 | | |
| Lovastatin + Pravastatin | 6506 | 72 ± 1 | 3.8 | 2.2 | 4.7 | 8.2 | 0.002 | | |
| Simvastatin | 3580 | 71 ± 3 | 11.2 | N/A | 8.1 | 11.2 | 0.002 | <0.005 | −11 to −4 |
| Captopril | 4616 | 73 ± 2 | 10.6 | 8.4 | 13.6 | 10.6 | 0.002 | <0.0005 | −10 to −4 |
| Furosemide | 15106 | 74 ± 1 | 8.9 | 9.0 | 16.7 | 14.1 | 0.001 | <0.0005 | −8 to −3 |
| Atenolol | 5340 | 72 ± 2 | 14.8 | 7.1 | 19.2 | 19.0 | 0.002 | <0.0005 | −14 to −8 |
| Metoprolol | 3799 | 72 ± 2 | 12.1 | 4.4 | 15.3 | 12.4 | 0.002 | <0.0005 | −12 to −5 |
| Propanolol | 1256 | 72 ± 2 | 17.5 | 3.9 | 42.4 | 20.7 | 0.002 | <0.0005 | −18 to −9 |
| Beta comb. | 10395 | 72 ± 2 | 14.1 | 5.9 | 22.8 | 16.6 | 0.002 | <0.0005 | −13 to −7 |
| Total # of Patients | 56790 | 74 ± 1 | 12.8 | 8.1 | 11.7 | 29.0 | 0.001 | <0.0005 | −8 to −3 |

Data from the three sites were combined to obtain an overall prevalence. Combined Prevalence refers to the total number of patients carrying the diagnosis of AD in comparison to the total number of patients on that particular medication. No patients on simvastatin were recorded at Hines. The Total # of Patients refers to the total number of patients in the databases less the number of patients on lovastatin or pravastatin. Mean Ages is the mean of the mean ages from each site. The significance (P vs. P/L) was determined by chi square analysis with respect to the combined pool of Lovastatin and Pravastatin (Lovastatin + Pravastatin).

The mean age of the patients (60 years or over) did not differ significantly among the eight medications (Table I). Gender did differ significantly between the sites, with the patients at both the Hines and Phoenix Veterans Authority Medical Centers being over 95% male, while the patients at Loyola Medical Center were 46.5% male. These differences, however, did not appear to affect the results of the study.

The total number of patients having an AD diagnosis, both on and off the medications studied, was 753. The overall rate of diagnosis of AD for the total sample size in all three databases (1.28%) was well below the estimated prevalence in the elderly given in other studies (Bachman et al., "Incidence of dementia and probable Alzheimer's disease in a general population: The Framingham study," *Neurology*, 43:515–9 (1993).) This could be due to differences in the ages of the cohorts among the studies.

Analysis of the combined data showed an unexpected dramatic reduction of 69.6% in the risk of AD, apparent degree of AD, and prevention of onset of AD for patients taking lovastatin or pravastatin, as compared to the total patient population. The risk of AD for patients taking lovastatin or pravastatin was also reduced in comparisons with the risk of AD for patients taking the other medications in the study. This overall pattern was repeated at each site. At each of the three sites, patients taking lovastatin or pravastatin also had a lower prevalence of AD than patients taking beta-blockers, furosemide, or captopril (Table I). However, to maximize the statistical power of the analysis, the data from the three sites were combined. This was justified because of the similar diagnostic trends and similar ages of the patient populations.

No such reductions in the rate of AD, apparent degree of AD, or prevention of onset of AD was found for patients taking simvastatin. Patients on simvastatin had a prevalence of AD that did not differ significantly from that of the total patient population or from that of patients taking captopril or furosemide.

Study Controls

The study had two different controls for potential selection biases. One was to compare the risk of AD in patients on statins (i.e., lovastatin, pravastatin, simvastatin) to patients on other medications related to heart disease and hypertension to compensate for potential errors in assessment of the total number of patients in the database and to provide a comparison between patients on statins and patients who may have a similar a priori risk of AD due to hypertension or heart disease. This comparison also controls for potential biases that could occur if clinicians were reticent to refer patients being treated for vascular diseases for a neurological work-up for AD. The study showed that patients taking lovastatin or pravastatin had a risk of AD that was 73% lower than those taking beta-blockers, 64.2% lower than those taking captopril, and 57.3% lower than those taking furosemide (Table I).

The second control was to examine the risk of TIAs in patients on the eight medications studied to control for other selection biases, such as the tendency of internists to refer patients for neurological work-ups. The study found that none of the medications, including the HMG CoA reductase inhibitors, had any effect on reducing the rate of TIAs in the patient population examined. In fact, the prevalence of TIAs increased for all of the medications as compared to the total patient population, likely reflecting the fact that TIA is the result of vascular disease. The patients receiving any of the medications examined would have an increased risk of vascular disease.

CONCLUSIONS

The study clearly showed that patients taking one or more HMG CoA reductase inhibitors had a dramatically lower risk of AD, thus indicating prevention of AD and treatment of existing AD, than the total population. Normally, a higher rate of AD would be expected for this population because of the presence of one risk factor for AD (elevated cholesterol) and the increased likelihood of a second risk factor (heart disease). For the patients taking beta-blockers, and hence having the risk factor of heart disease, the risk of AD was higher than the total population. The degree of reduction found in this patient population (69.6%) compares favorably with other putative AD therapeutics: estrogen (25–31%); NSAIDs (0% to 60%); and alpha-tocopherol (52%).

The study unexpectedly found that not all HMG CoA reductase inhibitors will function to decrease the risk of AD, as it was shown that simvastatin did not reduce the risk of AD. Simvastatin is as effective as pravastatin or lovastatin in lowering serum cholesterol and more effective in crossing the blood-brain barrier than pravastatin. Thus HMG CoA reductase inhibitors, such as lovastatin and pravastatin, may affect Alzheimer's disease for reasons other than merely lowering serum cholesterol.

The disclosures of all U.S. patents referenced above are specifically incorporated by reference.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A method for treating, preventing, or reducing the risk of Alzheimer's disease (AD) in a patient who has one or more risk factors for AD, comprising administering to a patient in need thereof a therapeutically effective amount of one or more inhibitors of the enzyme 3-hydroxy-3-methylglutaryl coenzyme A (HMG CoA) reductase, wherein:

(a) the HMG CoA reductase inhibitor is not simvastatin
   (b) treatment results in a reduction or inhibition of onset of Alzheimer's disease,
   (c) the one or more risk factors are selected from the group consisting of hypercholesterolemia, coronary artery disease, family or previous history of coronary artery disease, hypertension, diabetes, cigarette smoking, cerebrovascular disease, cardiovascular disease, elevated serum cholesterol, heart disease, and male gender, and
   (d) the patient to be treated does not possess the APOE 4 gene.

2. The method of claim 1, wherein said inhibitor of the enzyme HMG CoA reductase is selected from the group consisting of atorvastatin, rivastatin, mevastatin, lovastatin, pravastatin, velostatin, fluvastatin, and a combination thereof.

3. The method of claim 1, wherein said inhibitor of the enzyme HMG CoA reductase is selected from the group consisting of a pyrazole analog of a mevalonolactone, an indene analog of mevalonolactone, a 3-carboxy-2-hydroxy-propane-phosphinic acid derivative, a 6-[2-(substituted-pyrrol-1-yl)-alkyl]pyran-2-one, an imidazole analog of mevalonolactone, a heterocyclic analog of mevalonolactone, a naphthyl analog of mevalonolactone, an octahydro-naphthalene, fluindostatin, a keto analog of lovastatin, a 2,3-di-substituted pyrrole, furan, thiophene, and a combination thereof.

4. The method of claim 1, wherein the patient to be treated has hypercholesterolemia, with a serum total cholesterol concentration of at least about 5.2 mmol/liter (or at least about 200 mg/dl).

5. A method for treating, preventing, or reducing the risk of Alzheimer's disease (AD) in a patient who has one or more risk factors for AD, comprising administering to a patient in need thereof a therapeutically effective amount of one or more inhibitors of the enzyme 3-hydroxy-3-methylglutaryl coenzyme A (HMG CoA) reductase, wherein:

(a) the HMG CoA reductase inhibitor is not simvastatin,
   (b) treatment results in a reduction or inhibition of onset of Alzheimer's disease,
   (c) the one or more risk factors are selected from the group consisting of being 60 years of age or older, being exposed to environmental factors predisposing a patient to AD; having the α-2-macroglobulin genotype, having the presenilin I mutation for familial AD, having the presenilin II mutation for familial AD, having the amyloid precursor protein (APP) missense mutation for familial AD, having a family history of AD, having prior infection by the herpes simplex virus, and having prior infection by chlamydia pneumoniae, and (d) the patient to be treated does not possess the APOE 4 gene.

6. The method of claim 1, wherein treatment results in a reduction or inhibition of onset of Alzheimer's disease within about twelve months of onset of treatment.

7. The method of claim 1, wherein the treatment results in a reduction or inhibition of onset of Alzheimer's disease within about six months of the onset of treatment.

8. The method of claim 1, wherein the HMG CoA reductase inhibitor is pravastatin.

9. The method of claim 1, wherein the HMG CoA reductase inhibitor is lovastatin.

10. The method of claim 1, wherein the HMG CoA reductase inhibitor is administered in single or divided doses of from about 0.5 to about 2000 mg/day.

11. The method of claim 1, wherein the risk factor is hypercholesterolemia and the HMG CoA reductase inhibitor is selected from the group consisting of pravastatin, lovastatin, and a combination thereof.

12. The method of claim 1, wherein the risk factor is hypercholesterolemia and said treatment causes a reduction or inhibition of onset of Alzheimer's disease within about twelve months of onset of treatment.

13. The method of claim 1, wherein the risk factor is hypercholesterolemia and the HMG CoA reductase inhibitor is pravastatin which is administered in an amount of from about 10 to about 100 mg per day.

14. The method of claim 1, wherein the risk factor is hypercholesterolemia and the HMG CoA reductase inhibitor is lovastatin which is administered in an amount of from about 10 to about 100 mg per day.

15. The method of claim 1, wherein the risk factor is hypercholesterolemia and prior to treatment the patient has a blood cholesterol level of from about 200 to about 300 mg/dl.

16. The method of claim 5, wherein said inhibitor of the enzyme HMG CoA reductase is selected from the group consisting of atorvastatin, rivastatin, mevastatin, lovastatin, pravastatin, velostatin, fluvastatin, and a combination thereof.

17. The method of claim 5, wherein said inhibitor of the enzyme HMG CoA reductase is selected from the group consisting of a pyrazole analog of a mevalonolactone, an indene analog of mevalonolactone, a 3-carboxy-2-hydroxy-propane-phosphinic acid derivative, a 6-[2-(substituted-pyrrol-1-yl)-alkyl]pyran-2-one, an imidazole analog of mevalonolactone, a heterocyclic analog of mevalonolactone, a naphthyl analog of mevalonolactone, an octahydro-naphthalene, fluindostatin, a keto analog of lovastatin, a 2,3-di-substituted pyrrole, furan, thiophene, and a combination thereof.

18. The method of claim 5, wherein treatment results in a reduction or inhibition of onset of Alzheimer's disease within about twelve months of onset of treatment.

19. The method of claim 5, wherein the treatment results in a reduction or inhibition of onset of Alzheimer's disease within about six months of the onset of treatment.

20. The method of claim 5, wherein the HMG CoA reductase inhibitor is pravastatin.

21. The method of claim 5, wherein the HMG CoA reductase inhibitor is lovastatin.

22. The method of claim 5, wherein the HMG CoA reductase inhibitor is administered in single or divided doses of from about 0.5 to about 2000 mg/day.

* * * * *